United States Patent [19]

Negus et al.

[11] Patent Number: 5,509,822
[45] Date of Patent: Apr. 23, 1996

[54] ECG MONITOR SYSTEM

[75] Inventors: Charles C. Negus; Stephen J. Linhares, both of Taunton; Robert I. Rudko, Holliston, all of Mass.

[73] Assignee: PLC Medical Systems, Inc., Milford, Mass.

[21] Appl. No.: 454,008

[22] Filed: May 30, 1995

Related U.S. Application Data

[63] Continuation of Ser. No. 166,697, Dec. 14, 1993.

[51] Int. Cl.⁶ .................................................. H01R 11/00
[52] U.S. Cl. ............................ 439/502; 439/909; 128/642
[58] Field of Search ................................ 439/502–506, 439/909; 128/642, 639, 696, 733

[56]                References Cited

U.S. PATENT DOCUMENTS

| | | | |
|---|---|---|---|
| 2,197,910 | 4/1940 | Ament | 439/502 |
| 3,092,430 | 6/1963 | Miller | 439/502 |
| 3,895,635 | 7/1975 | Justus et al. | 439/909 |
| 4,632,121 | 12/1986 | Johnson et al. | 439/502 |
| 4,696,527 | 9/1987 | Ding et al. | 439/502 |
| 5,117,978 | 6/1992 | Blumenfeld et al. | 128/642 |
| 5,161,533 | 11/1992 | Prass et al. | 128/642 |
| 5,170,788 | 12/1992 | Blumenfeld | 128/642 |
| 5,203,720 | 4/1993 | Zini | 439/502 |
| 5,397,344 | 3/1995 | Garfield et al. | 128/642 |

FOREIGN PATENT DOCUMENTS

| | | | |
|---|---|---|---|
| 0403215 | 1/1946 | Italy | 439/502 |

*Primary Examiner*—Hien D. Vu
*Attorney, Agent, or Firm*—Iandiorio & Teska

[57]                ABSTRACT

A unitary ECG monitor lead and needle electrode system includes a connector for connection to an ECG monitor junction; an electrode lead interconnected with the connector at one end of the electrode lead, the lead including a signal conductor; and a needle electrode unit interconnected with the other end of the electrode lead and including a needle electrode, a body portion for receiving the other end of the lead and for receiving an electrode needle, for forming the needle electrode unit as a single integral unit.

5 Claims, 3 Drawing Sheets

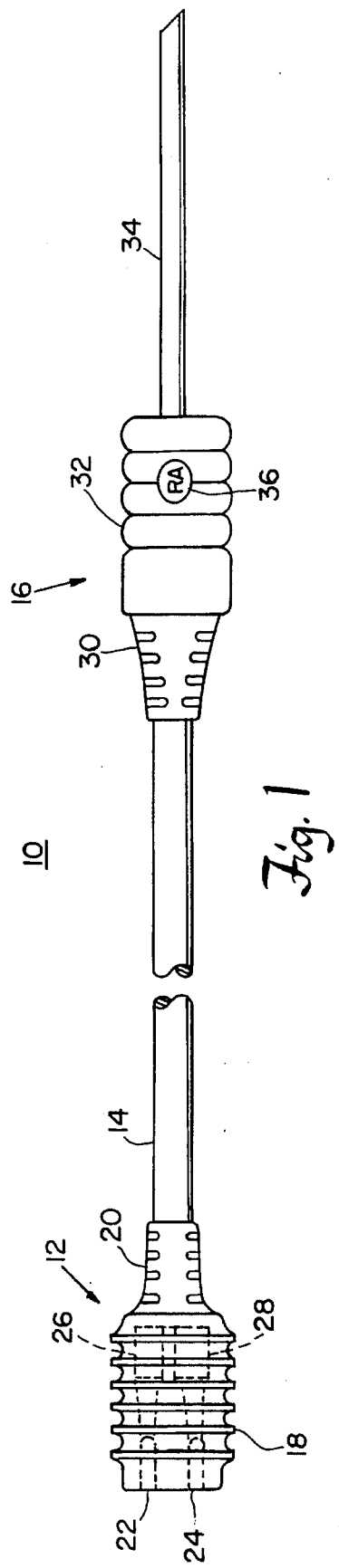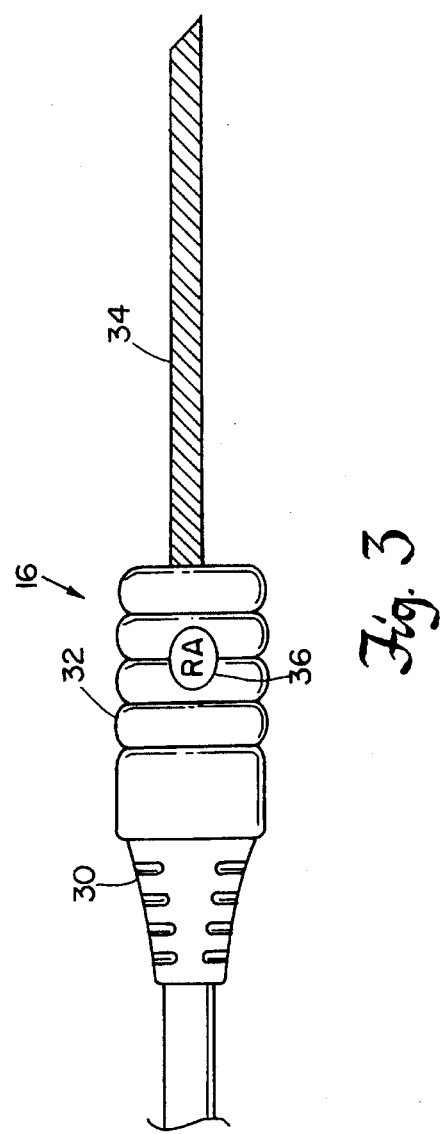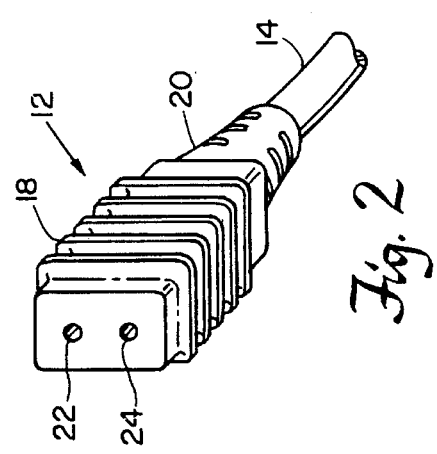

1

ECG MONITOR SYSTEM

This is a continuation of application Ser. No. 08/166,697, filed Dec. 14, 1993.

FIELD OF INVENTION

This invention relates to an improved ECG monitor lead and needle electrode system.

BACKGROUND OF INVENTION

Conventional electrode systems used, for example, with ECG monitors, employ a cable adapted at one end for connection to the ECG and at the other end contains a junction which receives a number, typically as many as five, lead wires that snap connect to pad electrodes which are attached to the skin of the patient. These electrode pads have a number of shortcomings, for example, when used with obese people whose subcutaneous fat is a good insulator or when used with animals whose fur prevents good contact. In such cases needle electrodes are used. The needle electrode is inserted into the body of a patient to convey ECG signals from the patient to the ECG monitor. Fewer needle electrodes can be used because needle electrodes are generally superior to the pad electrodes. Typically up to three needle electrodes are used so the junction is smaller to receive only three lead wires. However, each lead wire must terminate in a luer adapter which mounts a luer by means of a set screw or the like. This requires a manual labor step. In addition, the needle, typically a hypodermic needle, must be swaged shut at its distal end to prevent blood or other body fluids from backing up the hollow needle and contacting unsterile parts of the luer, luer adapter or lead. And further labor is required to remove the needle after each use for sterilization and reinstallation after sterilization. In addition to employing significant expensive labor time such hypodermic needle electrodes are themselves expensive.

SUMMARY OF INVENTION

It is therefore an object of this invention to provide an improved ECG monitor lead and needle electrode system.

It is a further object of this invention to provide such an improved ECG monitor lead and needle electrode system in which the lead and needle electrode unit are of integral construction.

It is a further object of this invention to provide such an improved ECG monitor lead and needle electrode system which is less expensive to make and maintain.

It is a further object of this invention to provide such an improved ECG monitor lead and needle electrode system which is entirely sterilizable as a unit.

It is a further object of this invention to provide such an improved ECG monitor lead and needle electrode system which does not require expensive standard hollow needles with luer hubs.

The invention results from the realization that a truly less expensive, more reliable and safer ECG monitor lead and needle electrode system can be effected by forming the needle electrode, body and end of the lead integrally as a single unit to avoid the need for luers, luer adapters and conventional hypodermic needles with luer hubs.

This invention features a unitary ECG monitor lead and needle electrode system. There is a connector for connection to an ECG monitor junction and an electrode lead interconnected with the connector at one end of the electrode lead. The lead includes a signal conductor. There is also a needle electrode unit interconnected with the other end of the electrode lead and including a needle electrode, a body portion for receiving the other end of the lead and for receiving an electrode needle for forming said needle electrode unit as a single integral unit.

In a preferred embodiment the needle electrode may be hollow, there may be a shield in the lead surrounding the signal conductor, and the shield may terminate in the body portion. The signal conductor may be electrically connected to the needle electrode in the body portion. The connector which interconnects with the ECG monitor junction may be integrally formed with the lead.

DISCLOSURE OF PREFERRED EMBODIMENT

Other objects, features and advantages will occur to those skilled in the art from the following description of a preferred embodiment and the accompanying drawings, in which:

FIG. 1 is a side elevational view of a unitary ECG monitor lead and needle electrode system according to this invention;

FIG. 2 is a perspective view of the ECG junction connector of FIG. 1;

FIG. 3 is a side elevational view with the needle shown in cross section of the needle electrode unit of FIG. 1;

Figure 4:
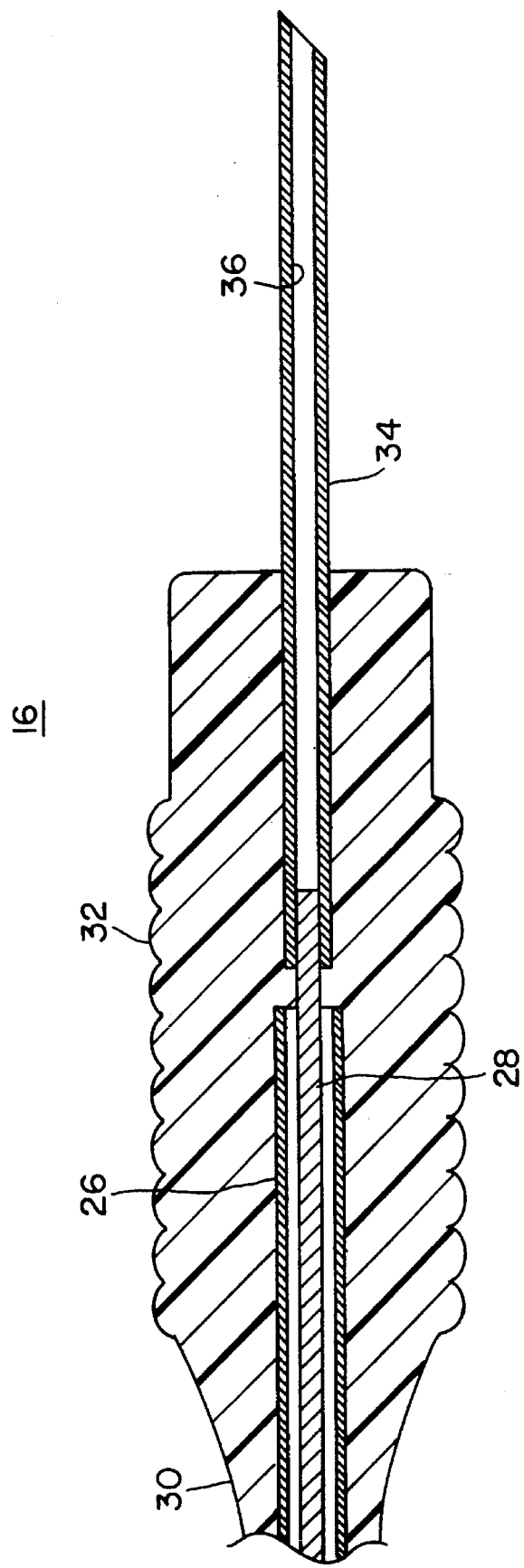
FIG. 4 is an enlarged cross-sectional side elevational view of the needle electrode unit of FIG. 1 shown with a hollow needle electrode.

This invention may be accomplished using a unitary ECG monitor lead and needle electrode system which includes a connector for connection to an ECG monitor junction. Typically the connector is an injection-molded plastic element made of polyethylene or some other suitable plastic and includes a body portion and a strain relief portion integrally connected with a lead. The lead may be shielded or unshielded. The other end of the lead, typically six feet long in the environment of ECG monitors, is connected with a needle electrode unit. The needle electrode unit includes a body portion which receives the lead integrally at one end and at the other end receives the electrode needle to form a single integral unit. The signal conductor of the lead is electrically connected with the electrode needle inside of the body portion, and if the lead is a shielded lead the shield terminates within that body portion. The needle electrode itself may be hollow or solid.

There is shown in FIG. 1 a unitary ECG monitor lead and needle electrode system 10 according to this invention which includes a connector 12 for connection to an ECG monitor junction box, a lead 14 typically up to six feet in length, and a needle electrode unit 16. Connector 12 is typically an injection molded plastic such as polyethylene or the like which has a ribbed body portion 18 and a strain relief portion 20. There are two female sockets 22 and 24, FIG. 2, at the end of connector 12 which electrically interconnect with a shield 26 and signal conductor 28, respectively, of lead 14. Lead 14 may be typically coated with a plastic jacket such as polyethylene or polyurethane. Needle electrode unit 16 at the other end of lead 14 is also made of an injection molded plastic and includes a strain relief area 30 and a body portion 32, FIG. 3. Electrode needle 34 is solid and is integral with and extends outwardly from body portion 32. If lead 14 were an unshielded cable, female socket 22 would be eliminated. Body 32 may include a placement indicator 36 bearing a legend such as "RA" which indicates "right arm" for the placement of the needle electrode 34.

Needle electrode unit 16 is shown in greater detail in FIG. 4, where shield 26 can be seen as terminating within body portion 32 and signal conductor 28 can be seen to electrically connect with needle electrode 34. As shown in FIG. 4, needle electrode 34 is hollow having a tubular bore 36 through its central portion similar to conventional hypodermic needles, but electrode needle 34 does not include the usual luer hub.

Figure 5:
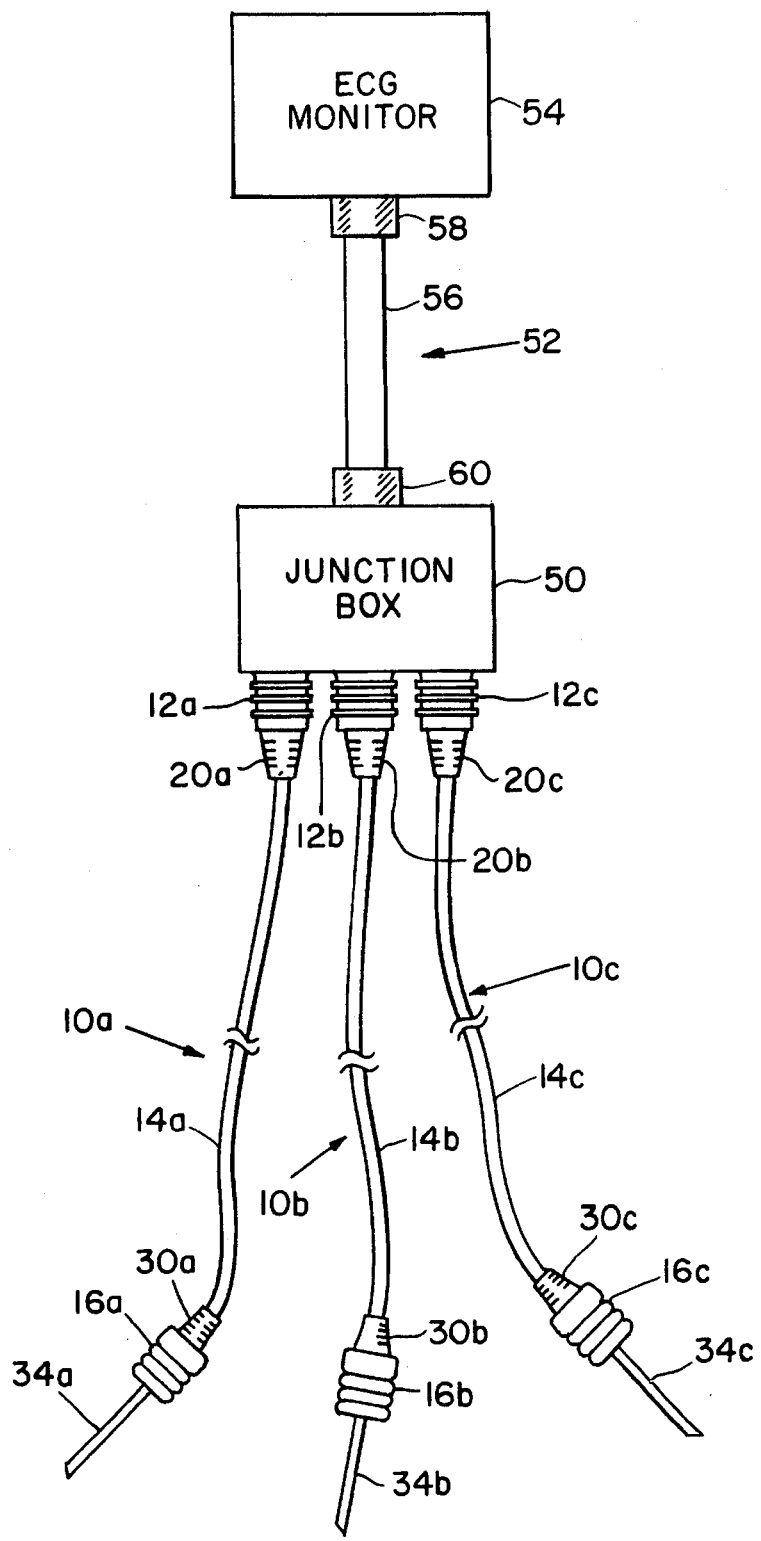
FIG. 5 is a schematic block diagram of a plurality of unitary ECG monitor leads and needle electrode systems connected to an ECG monitor and junction.

A plurality of unitary ECG monitor lead and needle electrode systems 10a, 10b and 10c, FIG. 5, according to this invention are typically employed by plugging into a junction 50 which is interconnected by a cable system 52 to a conventional ECG monitor 54. Cable system 52 includes a conventional cable 56 with end connectors 58 and 60. Junction box 50, typically includes three single pins or three pairs of pins in the case of shielded leads for receiving the connectors 12a, 12b and 12c of unitary ECG monitor lead and needle electrode systems 10a, 10b and 10c. If junction 50 is disposed in the ECG monitor itself, cable system 52 can be eliminated.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An ECG monitoring system comprising:

an ECG monitor;

a plurality of needle electrode systems each comprising:

a connector connecting to an ECG monitor junction, a single integral needle electrode unit, and a lead connecting said connector with said needle electrode unit forming said needle electrode system as a single integral unit, said lead including a signal conductor;

said connector having female sockets and a first end of said signal conductor, said single integral needle electrode unit comprising:

a body portion, and an electrode needle extending from said body portion and being molded into said body portion for permanently attaching the electrode needle in the body portion, a second end of said signal conductor electrically contacting said needle within said body portion, wherein said electrode needle can be inserted in the body of a patient to convey ECG signals from the patient to the ECG monitor.

2. The system of claim 1 in which said needle electrode is hollow, the second end of said signal conductor extending partially within said hollow needle.

3. The system of claim 1 in which said lead further includes a shield surrounding said signal conductor, a first end of said shield in said connector, a second end of said shield terminating within said body portion.

4. The system of claim 1 in which said connector is integrally formed with said lead.

5. The system of claim 1 in which said body portion is integrally formed with said lead.

* * * * *